(12) United States Patent
Hall et al.

(10) Patent No.: US 6,652,517 B1
(45) Date of Patent: *Nov. 25, 2003

(54) ABLATION CATHETER, SYSTEM, AND METHOD OF USE THEREOF

(75) Inventors: Jeffrey A. Hall, Birmingham, AL (US); Bruce H. KenKnight, Maple Grove, MN (US); G. Neal Kay, Birmingham, AL (US); Gregory P. Walcott, Wilsonville, AL (US); Wade A. Bowe, Temecula, CA (US)

(73) Assignee: UAB Research Foundation, Birmingham, AL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/558,478

(22) Filed: Apr. 25, 2000

(51) Int. Cl.[7] .............................. A61B 18/18; A61N 1/05
(52) U.S. Cl. ............................. 606/41; 606/49; 607/122
(58) Field of Search .............................. 606/59, 49, 48, 606/45, 41; 607/107, 122

(56) References Cited

U.S. PATENT DOCUMENTS

| | | | |
|---|---|---|---|
| 5,687,723 A | 11/1997 | Avitall | |
| 5,690,611 A | 11/1997 | Swartz et al. | |
| 6,004,269 A | 12/1999 | Crowley et al. | |
| 6,012,457 A | 1/2000 | Lesh | |
| 6,270,496 B1 | 8/2001 | Bowe et al. | |
| 6,325,797 B1 | * 12/2001 | Stewart et al. | ................. 606/41 |
| 6,332,880 B1 | * 12/2001 | Yang et al. | ................. 604/528 |

FOREIGN PATENT DOCUMENTS

WO     WO 99/02096     1/1999

OTHER PUBLICATIONS

Calkins, Hugh, et al., *A New System for Catheter Ablation of Atrial Fibrillation*, The American Journal of Cardiology, vol. 83, No. 5B, pp. 227D–236D (Mar. 11, 1999).
PCT International Search Report, International Application No. PCT/US01/05592.

* cited by examiner

*Primary Examiner*—Linda C. M. Dvorak
*Assistant Examiner*—Kenneth G Schopfer
(74) *Attorney, Agent, or Firm*—Myers Bigel Sibley & Sajovec

(57) ABSTRACT

A cardiac ablation apparatus for producing a circumferential ablation that electrically isolates a heart chamber wall portion from vessel such as a pulmonary vein extending into a wall portion comprises (a) an elongate centering catheter having a distal end portion; (b) an expandable centering element connected to the centering catheter distal end portion and configured for positioning within the vessel when in a retracted configuration, and for securing the elongate centering catheter in a substantially axially aligned position with respect to the vessel when the centering element is in an expanded configuration; (c) an ablation catheter slidably connected to the centering catheter the ablation element having a distal end portion, and (d) an expandable ablation element connected to the ablation catheter distal end portion.

20 Claims, 9 Drawing Sheets

ABLATION CATHETER, SYSTEM, AND METHOD OF USE THEREOF

FIELD OF THE INVENTION

The present invention concerns ablation catheters and systems useful for the treatment of cardiac arrhythmias, and particularly atrial arhythmias.

BACKGROUND OF THE INVENTION

Atrial fibrillation is one of the most common cardiac arrhythmia. Health consequences associated with atrial fibrillation include decreased cardiac output, less regular ventricular rhythm, the formation of blood clots in the atrial appendages, and an increased incidence of stroke. While some drugs are available for the treatment of atrial fibrillation, they have a number of side effects which reduce their therapeutic utility.

Atrial fibrillation may be treated by the "maze procedure". The maze procedure is a surgical technique that involves the formation of a pattern of incisions in the left and/or right atrial walls. This procedure is intensely invasive with a difficult recovery, and it has accordingly been desirable to establish less invasive, closed-heart, catheter based techniques for treating atrial fibrillation.

Swartz et al., U.S. Pat. No. 5,690,611, describes a process for the treatment of atrial arrhythmia in which a catheter is introduced into the left or right atrium through a guiding introducer and a pattern of ablation tracks formed therein. A problem with this technique is that an extensive number of lengthy ablation tracks are formed, and since linear lines are formed by slowly dragging the catheter procedure time is extensive.

Avitall, U.S. Pat. No. 5,687,723, describes a mapping and ablation catheter for treating atrial fibrillation. The device is designed to produce linear lesions from an array of mapping and ablation electrodes serially positioned along the catheter. A vascular guide wire is included fixed to the distal tip of the catheter to help navigate the device. The hook-shaped vascular guide wire may be inserted into a pulmonary vein and anchored therein, apparently by a hooking action, to help adjust the electrode-carrying segment of the catheter (FIGS. 14–15; column 9). However, Avitall still necessitates elongate linear lesions in the manner described by Swartz et al.

H. Calkins et al., *Am. J. Cardiol.* 83, 227D–236D (1999), describes a system that incorporates multiple preshaped steerable catheters. The pre-shaped steerable catheters are formed by embedding a preshaped Nitinol stylet in the shaft thereof. The catheters can deliver a variety of lesion shapes, from localized spot lesions to lesions that are 8 centimeters in length.

Recent studies have suggested that focal arrhythmia can originate from a tissue region along the pulmonary veins extending from the left atrium, particularly the superior pulmonary veins. For example, Lesh et al., U.S. Pat. No. 6,012,457, provide a device that forms a circumferential lesion and circumferential conduction block in a pulmonary vein. The device is a balloon that carries a circumferential electrode, and extends over a guidewire through the atrium and into, or partially into, a vein. The balloon centers and secures the device in the vein, where the electrode ablates a circumferential region of tissue within the vein, or within the vein and extending out into the atrium. While this device reduces the amount of tissue that must be ablated to a smaller circumferential pattern, a problem with this approach is that the ablation of tissue within the vein can lead to pulmonary vein stenosis, which may induce pulmonary hypertension. See, e.g., I. Robbins et al., *Circulation* 98, 1769 (1988); G. Taylor et al., Pace 22 (Part II), 712 (1999).

Accordingly, an object of this invention is to provide a closed-heartprocedure for treating atrial arrhythmia in which the region of tissue ablation is reduced, yet the ablation of tissue within a pulmonary vein is avoided.

SUMMARY OF THE INVENTION

A first aspect of the present invention is a cardiac ablation catheter apparatus for producing a circumferential ablation that electrically isolates an inner wall portion (e.g., an atrial wall portion) of a heart from a connecting vessel or orifice therein (e.g., a pulmonary vein extending into an atrial wall portion). The apparatus comprises:

(a) an elongate centering catheter having a distal end portion;

(b) an expandable centering element connected to the centering catheter distal end portion and configured for positioning within the vessel (e.g., the pulmonary vein) when in a retracted configuration, and for securing the elongate centering catheter in a substantially axially aligned position with respect to the vessel when the centering is in an expanded configuration;

(c) an ablation catheter slidably connected to the centering catheter the ablation element having a distal end portion, and (d) an expandable ablation element connected to the ablation catheter distal end portion, the ablation element configured to form a circumferential ablation on the wall portion around the elongate centering catheter when the centering catheter is axially aligned with respect to the vessel.

The expandable centering element may be any suitable device, including a balloon, an expandable cage or stent-like structure (referred to as a "stent" herein), a structure formed from a preformed stylet, etc. Likewise, the expandable ablation element may be any suitable device, including a balloon or stent, a structure formed from a preformed stylet, etc, with the ablation element carrying one or more ablation electrodes for ablating the target tissue. In another embodiment, the ablation element may comprise a plurality of expandable legs (e.g., at least three or four, up to eight, ten or more), with at least one of those expandable legs (optionally a plurality of those legs, and in one embodiment all of those legs) having an ablation electrode on a distal tip portion thereof. It will be appreciated that the ablation electrodes may be continuous or discontinuous around the vessel, with the circumferential ablation being formed by rotation of the ablation element when the electrodes are discontinuous.

In one embodiment of the invention, the centering catheter is slidably received on a guide wire, which guide wire serves to guide and place the centering catheter and then the ablation catheter into the appropriate heart chamber (e.g., the atrium). In another embodiment, the ablation catheter is itself a steerable catheter, incorporating a steering mechanism such as a preformed steering stylet operatively associated with a steering tendon.

A second aspect of the present invention is a cardiac ablation system for producing a circumferential ablation that electrically isolates a wall portion (e.g., an atrial wall portion) of a heart from a vessel such as a pulmonary vein extending into the wall portion, the system comprises a catheter as described above, with a power supply operably associated with the ablation element. Preferably, a first expansion actuator is operatively associated with the centering element, and a second expansion actuator operatively associated with the ablation element.

A third aspect of the present invention is a cardiac ablation method for producing a circumferential ablation that electrically isolates a wall portion such as an atrial wall portion of a heart from a vessel such as a pulmonary vein extending into the wall portion. The method comprises the steps of:

(a) inserting an elongate centering catheter having a distal end portion through an heart chamber such as an atrium into the vessel (e.g., a pulmonary vein), the distal end portion having an expandable centering element for engaging the vessel connected thereto;

(b) expanding the centering element in the vessel to secure the elongate centering catheter in a substantially axially aligned position with respect to the vessel; then (c) inserting an ablation catheter slidably connected to the centering catheter into the chamber, the ablation catheter having an expandable ablation element connected to the distal end portion thereof; then (d) positioning the ablation element on the chamber wall portion; and then (e) forming a circumferential ablation around the elongate centering catheter on the wall portion in the chamber and outside of the vessel. Preferably, the inner diameter of the circumferential ablation is greater than the inner diameter of the vessel.

Because the apparatus described above provides an ablation element that can be slidably positioned along the centering catheter, rather than rigidly linking the two, and (in a preferred embodiment) further provides an ablation element whose diameter can be adjusted within the chamber after the ablation element is inserted into the chamber, but before forming the circumferential ablation, the apparatus disclosed herein simplifies the formation of the chamber wall ablation without undue intrusion of the ablation into a vessel such as a pulmonary vein.

In an alternative embodiment of the invention, the centering element can be a nonexpandable, compliant centering element (e.g., an elastic finger), the centering element typically having an outer diameter that is not greater than, and preferably smaller than, the inner diameter of the vessel into which it is inserted. Such a centering element obviates the need for an expansion mechanism associated with the centering element and advantageously makes the device mechanically simpler. When a nonexpandable, compliant centering element is employed, then the ablation element is configured with the diameter of the electrodes sufficiently wide so that the ablation formed thereby is on the wall of the chamber and does not intrude into the vessel into which the centering element is inserted, regardless of lateral position of the centering element in that vessel.

Accordingly, a fourth aspect of the present invention is a cardiac ablation apparatus for producing a circumferential ablation that electrically isolates a chamber wall portion of a heart from a vessel extending into the wall portion, the apparatus comprising:

(a) an elongate catheter having a distal end portion;

(b) a nonexpandable, compliant, centering element as described above connected to the catheter distal end portion and configured for positioning within the vessel; and (c) an expandable ablation element connected to the catheter distal end portion, the ablation element configured to form a circumferential ablation on the wall portion around the centering element when the centering element is positioned in the vessel. The ablation element can be slidably connected to the catheter by providing a separate ablation catheter around a centering catheter as described above, or both the ablation element and the centering element can be permanently affixed (e.g., rigidly connected or integrally formed on) to the same catheter. The ablation element may be the same as any of those described above.

A fifth aspect of the present invention is a cardiac ablation system for producing a circumferential ablation that electrically isolates a chamber wall portion of a heart from a vessel extending into the wall portion, the system comprising:

(a) an elongate catheter having a distal end portion;

(b) a nonexpandable, compliant, centering element as described above connected to the catheter distal end portion and configured for positioning within the vessel; and (c) an expandable ablation element connected to the catheter distal end portion, the ablation element configured to form a circumferential ablation on the wall portion around the centering element when the centering element is positioned in the vessel; and (d) a power supply operably associated with the ablation element.

A sixth aspect of the present invention is a cardiac ablation method for producing a circumferential ablation that electrically isolates a chamber wall portion of a heart from a vessel extending into the wall portion, the method comprising the steps of:

(a) inserting an elongate catheter having a distal end portion through an chamber into the vessel, the distal end portion having a nonexpandable, compliant centering element as described above connected thereto, the centering element having an outer diameter smaller than the inner diameter of the vessel, the distal end portion further having an ablation element connected thereto;

(b) positioning the ablation element on the chamber wall portion; and then (c) forming a circumferential ablation around the centering element on the wall portion in the chamber and outside of the vessel.

The foregoing and other objects and aspects of the present invention are explained in greater detail in the drawings herein and the specification set forth below.

DETAILED DESCRIPTION OF THE PREFERRED EMBODIMENTS

The present invention is explained in greater detail below. This is intended as an illustrative explanation of the invention, and is not intended to be a detailed catalog of all possible embodiments of the invention, as numerous variations will be apparent to those skilled in the art. For example, while it is preferred that the invention be configured and used to ablate the atrial wall within an atrium around a pulmonary vein, the invention can be used in other chambers of the heart, to form ablation around other vessels entering those chambers.

Figure 1:
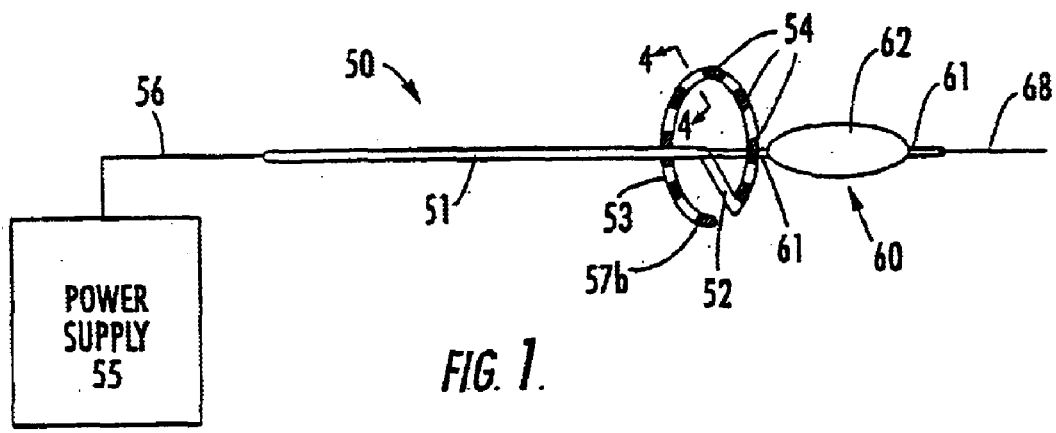
FIG. 1 illustrates a first embodiment of the present invention, in which the centering element comprises a balloon and the ablation element comprises a preformed stylet, and with the centering catheter slidably received on a guide wire.
Figure 4:
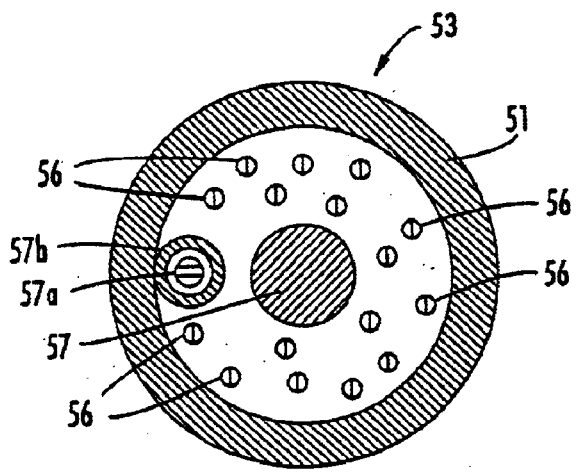
FIG. 4 is a cross section of the apparatus of FIG. 1, taken along line 4—4 of FIG. 1.

FIG. 1 and FIG. 4 illustrate a first embodiment of the present invention. The apparatus 50 comprises an ablation catheter 51 having a distal end portion 52, with a preformed expandable ablation element 53 in the form of a circle connected to the distal end portion. The expandable ablation element is collapsed when introduced into the atrium through an introducer sheath (not shown), and assumes the preformed position once it is inserted into the atrium free of the introducer sheath (see FIG. 10). A plurality of ablation electrodes 54 are connected to the ablation element, with the ablation electrodes operatively connected to a power supply 55 by appropriate wires 56 (shown individually in FIG. 4 and bundled in FIG. 1). The ablation catheter is slidably received over a centering catheter 60, which centering catheter has a distal end portion 61 to which is connected an expandable centering balloon 62. The centering catheter is, in turn, slidably received over a guide wire 68 to facilitate placement of the assembly into the appropriate location in a pulmonary vein and the left atrium.

As shown in FIG. 4, the expandable ablation element 53 contains a preformed stylet 57 in the body thereof, which is formed of a suitable elastic resilient material that has a memory for the preformed position, such as nitinol. The ablation catheter further contains an elongate tendon 57a, conveniently formed of stainless steel wire, running from an actuator or steering mechanism (not shown), running freely within internal sheath 57b through the ablation catheter and internally fixed to the end terminus 57c of the ablation element (see FIG. 1). The internal sheath is aligned along the internal (or external) circumference of the ablation element 53, so that increasing tension on the tendon increases the diameter of the ablation element. Other portions of the ablation catheter can be stiffened by incorporating a stiffening member (e.g., high durometer steel braid) into the catheter wall so that forces exerted through the tendon are primarily applied to changing the shape of the ablation element 53. Additional rigidity/stiffness can also be achieved through stiffening of the outer jacket material. A tendon and stylet system of this type can also be used to produce a steerable centering catheter, as described in connection with FIGS. 12–15 below, in which the distal portion of the centering catheter can be changed in shape (e.g., bent), by the application of tension to a steering tendon running laterally, or off-center, in the catheter body, through an internal sheath, and fixed to the distal tip of the catheter (note that the steering tendon need only be off center in the distal section of the catheter, and may run on the centerline in a proximal or intermediate section). Stylets as described herein may be formed of an alloy which exhibits a martensitic phase transformation. Such alloys include those which exhibit non-linear superelasticity (typically Ni—Ti with Ni at 49/51.5% atomic) and those which exhibit linear superelasticity (e.g., Ni—Ti in near equi-atomic composition which has been cold worked). Particularly preferred is a Ni-Ti alloy with 54–57% by weight of Ni. A preferred material for such stylets is nitinol. Of course, other steering systems may also be employed, such as temperature actuated shaped-memory materials. Thus, the steering actuator may be a mechanical actuator (e.g., one that applies and releases tension to a tendon) or an electrical actuator (e.g., on that applies an electrical current to heat a temperature actuated shaped-memory material).

Figure 2:
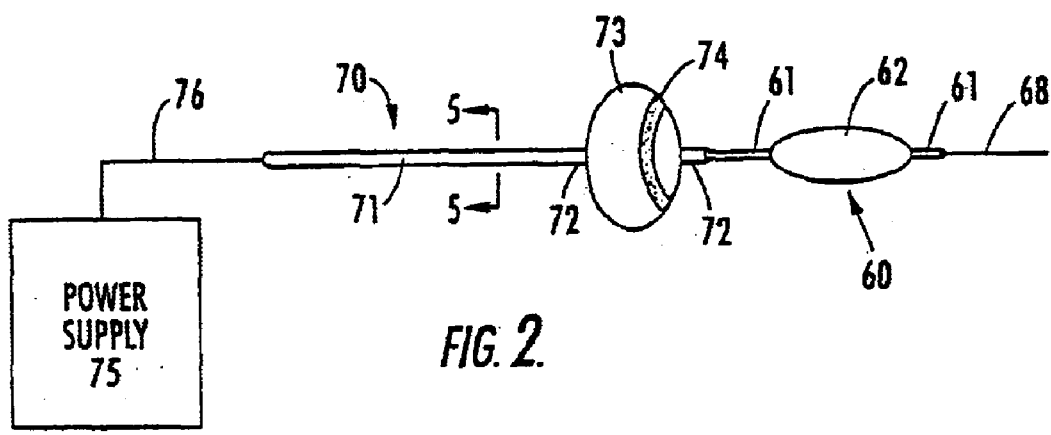
FIG. 2 illustrates a second embodiment of the invention, in which both the centering element and the ablation element comprise a balloon.
Figure 5:
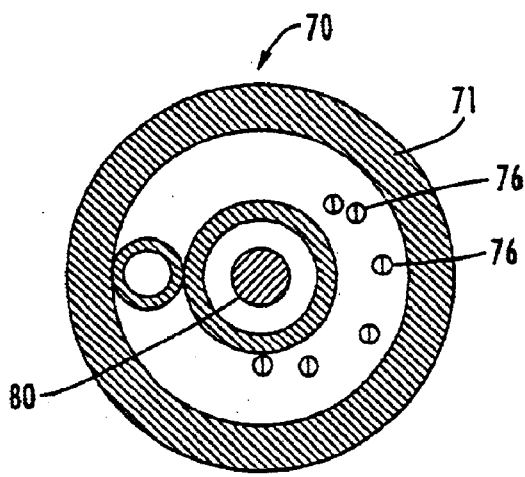
FIG. 5 is a cross section of the apparatus of FIG. 2, taken along line 5—5 of FIG. 2.

FIG. 2 and FIG. 5 illustrate a second embodiment of the invention. The apparatus 70 comprises an ablation catheter 71 having a distal end portion 72, with an expandable ablation element 73 in the form of a balloon connected to the distal end portion. The expandable ablation element is collapsed when introduced into the atrium through an introducer sheath (not shown), and is inflated into an enlarged form once it is inserted into the atrium free of the introducer sheath. An ablation electrode 74 is connected to the balloon, with the ablation electrode operatively connected to a power supply 75 by appropriate electrical wires 76. The ablation catheter is slidably received over the centering catheter as described above.

Figure 3:
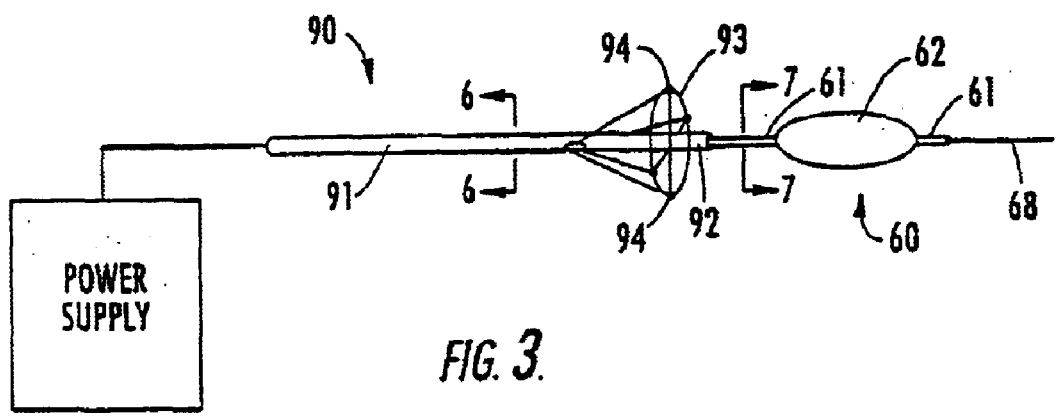
FIG. 3 illustrates a third embodiment of the invention, in which the centering element comprises a balloon and the ablation element comprises a stent.
Figure 6:
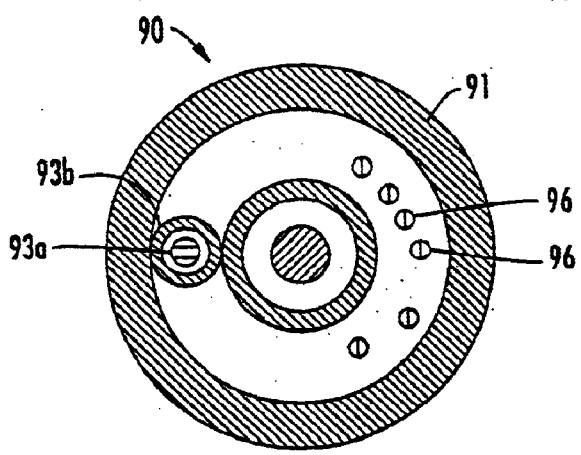
FIG. 6 is a cross section of the apparatus of FIG. 3, taken along line 6—6 of FIG. 2.
Figure 7:
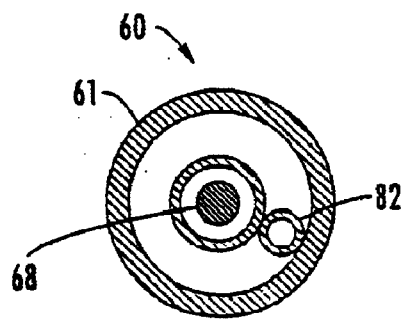
FIG. 7 is a cross section of the centering catheter of the apparatus of FIG. 3, taken along line 7—7 of FIG. 3.

FIG. 3 and FIG. 6 illustrate a third embodiment of the invention, with the centering catheter further illustrated in cross section in FIG. 7. The apparatus 90 comprises an ablation catheter 91 having a distal end portion 92, with an expandable ablation element in the form of an expandable stent 93 connected to the distal end portion. The expandable stent is collapsed when introduced into the atrium through an introducer sheath (not shown), and is opened into its operative configuration through an expansion tendon 93a contained within an internal sheath 93b within the catheter lumen. A plurality of ablation electrodes 94 are connected to the ablation element, with the ablation electrodes operatively connected to a power supply 95 by appropriate wires 96. The ablation catheter is slidably received over a centering catheter 60, as described above.

The ablation elements 53, 73, 93 above are optionally but preferably each connected to an expansion actuator (not shown) to increase or decrease the diameter of the ablation element appropriate to the particular target site for ablation. The centering elements 62 is likewise connected to an expansion actuator (not shown) to increase or decrease the diameter of the ablation element. Any type of expansion actuator may be employed, including mechanical, electrical, pneumatic and hydraulic actuators, depending upon the type of centering element or ablation element employed. When the element is a balloon, as is the case with centering balloon 62, then the actuator is typically a pneumatic or hydraulic expansion actuator, which is operatively connected to the centering balloon through line or tube 82 that extends through the centering catheter body (see FIG. 7). Because the diameter of the centering element is not linked or coupled to the diameter of the ablation element by mounting of the elements on separate catheters, the system of the invention is able to better accommodate a variety of anatomical configurations within the heart and avoid ablation within the coronary vein by maintaining the circumferential ablation formed outside of the pulmonary vein.

While the invention is illustrated above with a guide wire positioned through a lumen extending the length of the centering catheter, it will be appreciated that the lumen may extend only through a distal portion of the centering catheter, with a side port being located at a intermediate position on the catheter, to reduce the diameter of the proximal catheter. In addition, a "fixed" guide wire fixed to the distal end of the centering catheter, could be employed. Further, the guide wire could be eliminated entirely, particularly when a steerable centering catheter (as described below) is employed.

In general, the catheters of the invention can be inserted into the left or right atria of the heart, or the ventricles of the heart, by insertion of a catheter into a vein that leads to the heart, or through retrograde techniques in which a catheter is inserted into an artery that extends from the heart. Such insertion can be optionally be assisted by the placement of guide wires, introducer sheaths and the like, depending upon the particular surgical technique employed. For example, to insert a catheter of the invention into the right atrium of the heart, the venous system may be accessed by inserting a guiding catheter or an introducer sheath into a peripheral vein such as the femoral vein in accordance with known techniques, and then advanced through the vena cava and into the right atrium. Once in the right atrium, a guide wire can be inserted through the introducer sheath in accordance with known techniques and placed in a vein as desired.

To insert a catheter into the left atrium of the heart, an introducer sheath or guiding catheter is first introduced into the right atrium as described above, and then the septum or fossa ovalis between the right and left atrium is punctured and the introducer sheath or guiding catheter advanced through the puncture from the right atrium to the left atrium. Guide wires, guiding catheters and the like can then be advanced through the introducer sheath and into a pulmonary vein that enters the left atrium in the same manner as introduced into the right atrium.

Figure 8:
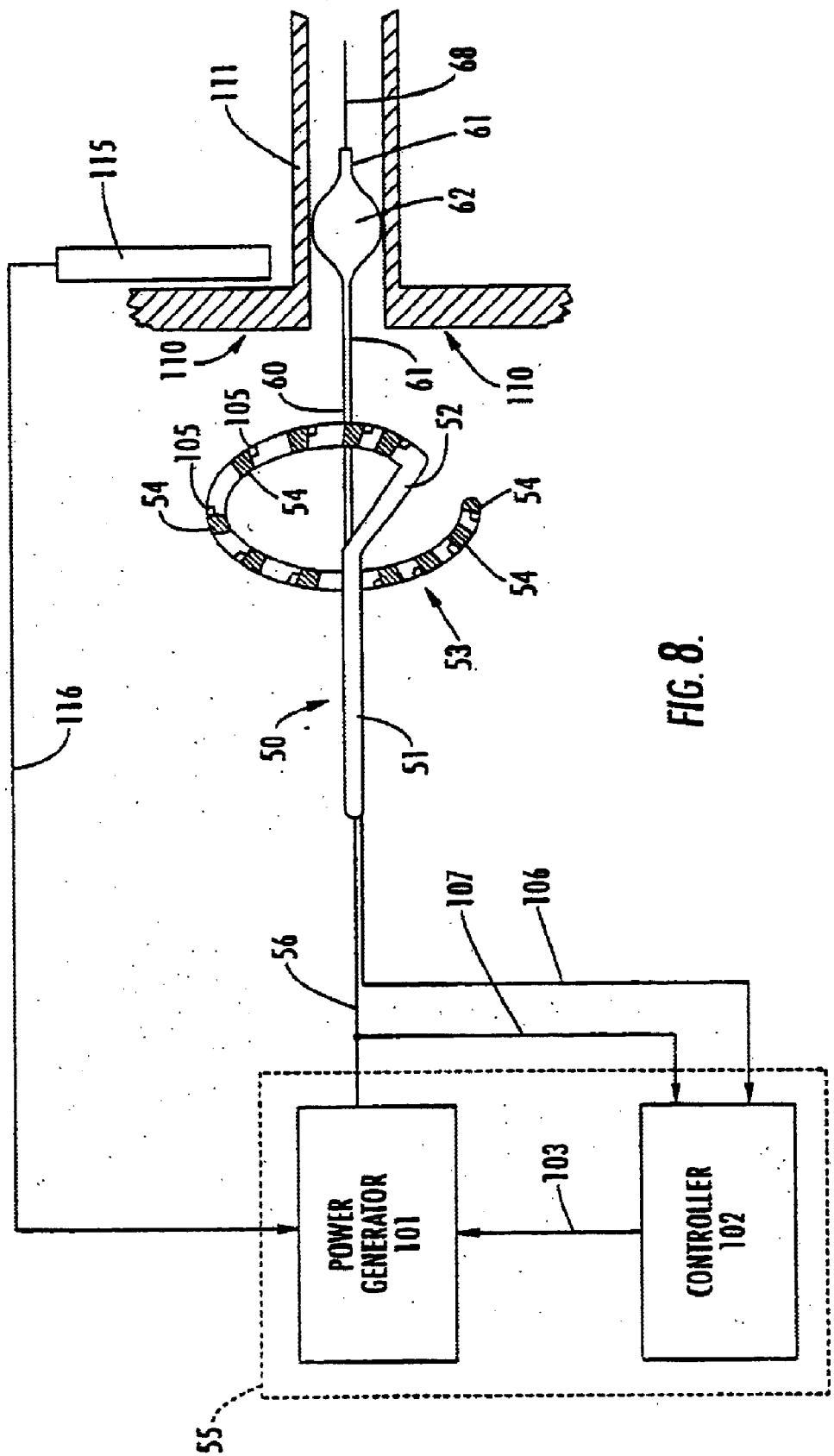
FIG. 8 is a schematic diagram of the apparatus of FIG. 1, illustrating its placement in a pulmonary vein entering into an atrium, and the completion of the electrical circuit for formation of the ablation.

FIG. 8 is a schematic diagram of one illustrative embodiment of the apparatus of FIG. 1, illustrating its placement in a pulmonary vein entering into an atrium, and the completion of the electrical circuit for formation of the ablation. The power supply 55 includes power generator 101, which is controlled by a controller 102 through output received by the power generator through control line 103. The output of the power supply may be through one or more channels, supplied along line 56 to the ablation electrodes 54. Further, the ablation element 53, in addition to carrying ablation electrodes 54, carries a plurality of temperature sensors 105, which are connected through one or a plurality of feedback lines 106 to the controller 102. In addition to monitoring temperature sensors 105, the controller can monitor the output of the power generator 101 through feedback line 107.

The target site for ablation 110 on the atrial wall is aligned by insertion of the centering catheter 60 into a selected vein 111, and the expansion of the centering balloon 62 within that vein. The electrical circuit is completed by a backplate 115 located proximal to and in electrical contact with the atrial wall to be ablated (e.g., by contacting the backplate to the chest of the subject), which backplate is in turn electrically connected to the power generator 101 through line 116. The backplate may be optional, as current paths can also be produced between electrodes on the ablation element, depending upon the particular power supply employed.

In a manual arrangement, the temperature sensed, and/or the impedance determined through the electrodes may be displayed to an operator. The operator in response may then manually control the duty cycle or other power parameters by controls associated with controller 102. Where multiple output channels are provided, multiple corresponding manual controls may also be provided.

In general, any power supply may be used, including but not limited to thermal ablation power supplies and radio frequency (RF) power supplies (which may also effect the ablation through thermal energy to the ablation site). One suitable power supplies is, for example, the Guidant HRT Linear Phased RF Ablation Generator (available from Guidant Corporation, Cardiac Rhythm Management Group, St. Paul, Minn., USA). This power supply is a multichannel RF generator capable of delivering phased RF energy at a frequency of 540 kHz to selected electrodes.

The ablation electrodes 54 are preferably a plurality of separate band electrodes that extend around the body portion of the distal catheter. Any number of band electrodes (e.g. 3–12) may be arranged on the distal catheter, with intervening space between each electrode, to form the ablation element. Even a single band electrode may be employed, with the circumferential ablation being formed by rotating the ablation electrode and imparting corresponding rotation to the ablation element. Also, while the ablation electrodes are preferably arranged in a linear array, any geometric arrangement of electrode or electrodes that can be used to create a circumferential ablation may be employed.

The ablation electrodes are preferably formed of a material having a sigificantly higher thermal conductivity than that of the target site for ablation 110. Examples of suitable materials include, but are not limited to, metals such as silver, copper, gold, chromium, aluminum, molybdenum, tungsten, nickel, platinum, and platinum/10% iridium. Because of the difference in thermal conductivity between the electrodes 54 and the ablation site 110, the electrodes cool off more rapidly in the flowing fluids within the atrium. The power supplied to the electrodes may accordingly be adjusted during ablation to allow for the cooling of the electrodes while at the same time allowing for the temperature of the tissue to increase to a point so that ablation results. Preferably, each electrode 54 is sized so that the surface area available for contact with fluid in the atrium is sufficient to allow for efficient heat dissipation from the electrodes to the surrounding fluid (e.g., blood). In one preferred embodiment, each electrode 54 is 5–9 French in diameter, and 1–6 millimeters in length. Preferably, each electrode 54 is 0.05 to 0.13 millimeters thick. The same parameters and dimensions may be applied to electrodes in other embodiments of the invention as described herein.

Figure 9:
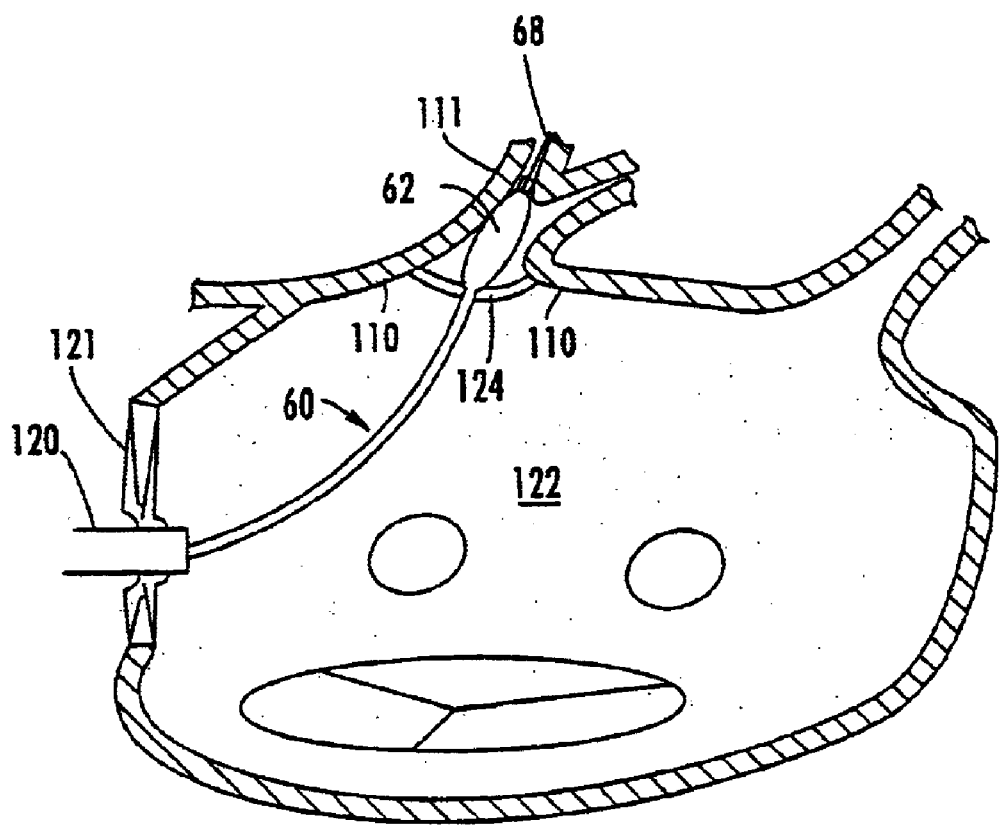
FIG. 9 illustrates the insertion of a guide (or "guiding") catheter into a pulmonary vein in the left atrium of a subject, in accordance with the present invention.
Figure 10:
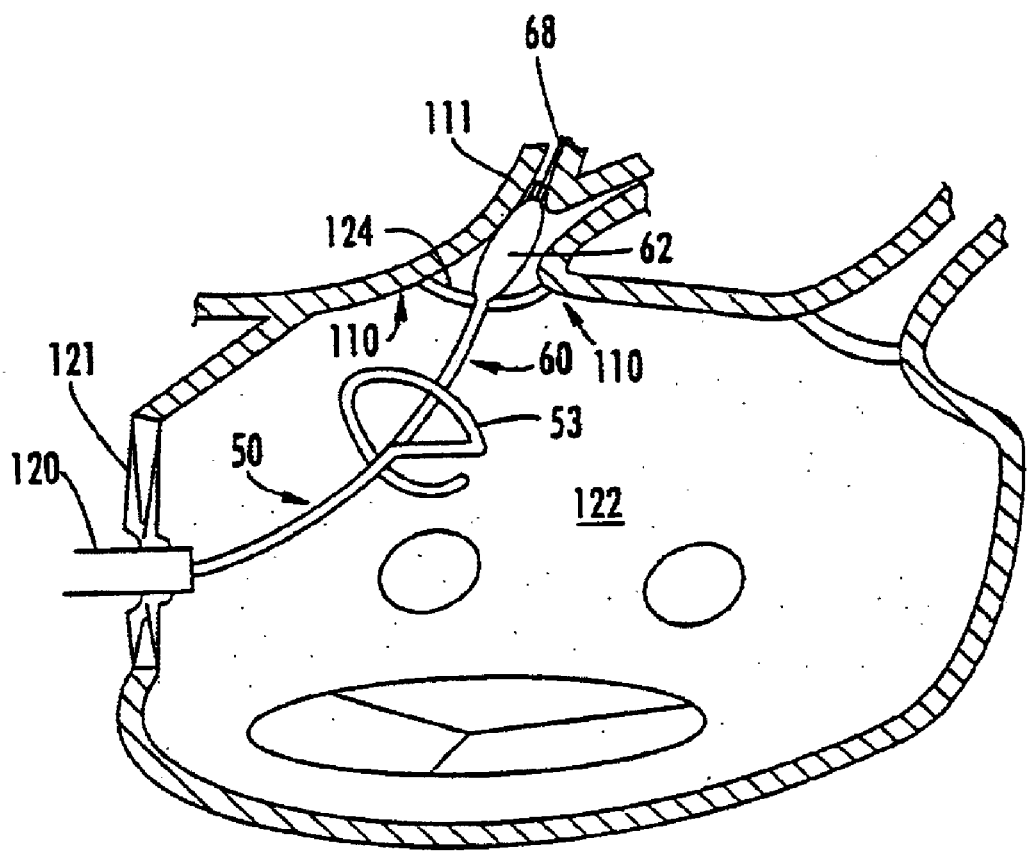
FIG. 10 illustrates the initial insertion of an ablation catheter into the left atrium of a subject, where the ablation element is caused to assume its active configuration for ablation, but prior to ablation.
Figure 11:
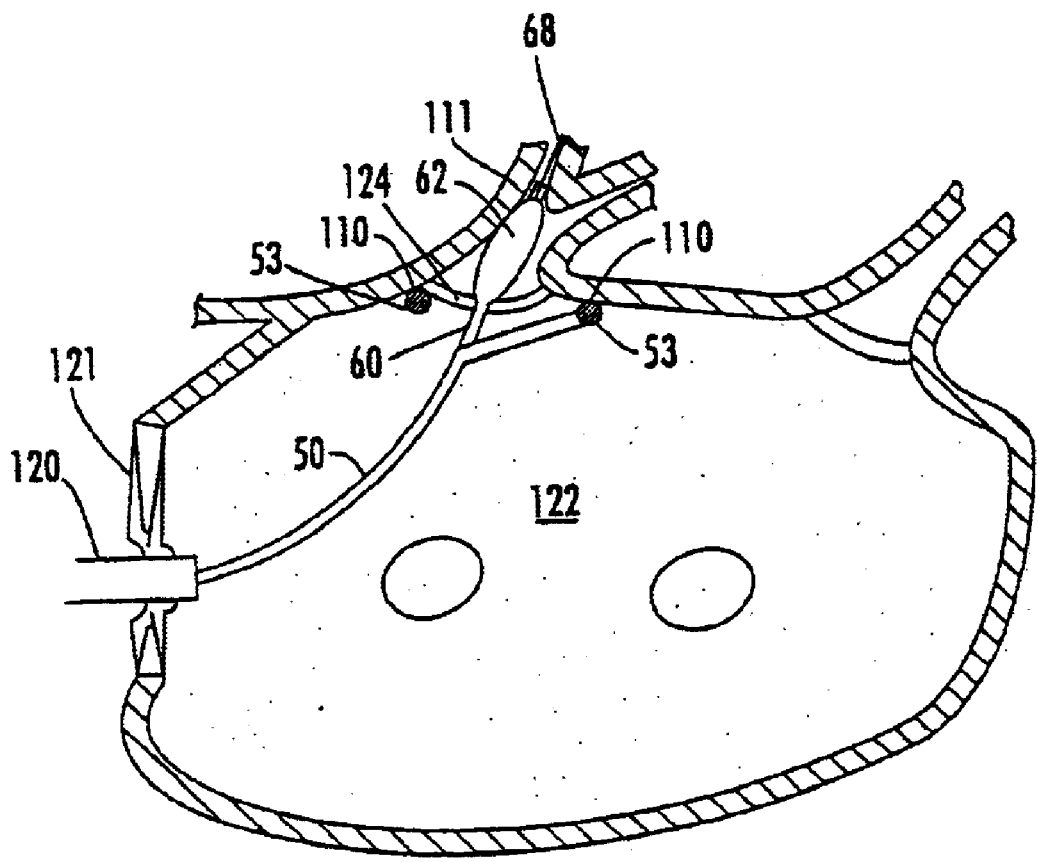
FIG. 11 illustrates the contacting of an ablation element of the invention to the atrial wall of a subject within the left atrium of a subject.

The method of the present invention, as practiced with an apparatus of FIG. 8, is illustrated in FIGS. 9–11. As shown in FIG. 9, an introducer sheath 120 is punctured through the septum 121 between the right atrium (not shown) and the left atrium 122 of the heart of a subject in accordance with known techniques. A guide wire 68 is then advanced into a pulmonary vein 111, also in accordance with known techniques, and a centering catheter 60 advanced over the guidewire and to the pulmonary vein so that the centering balloon 62 is positioned through the opening to the pulmonary vein 124 and within that pulmonary vein. The centering balloon is then expanded within the pulmonary vein to secure the centering catheter within the pulmonary vein as illustrated. In alternative embodiments, the centering catheter could be configured so that the guide wire only passes through a distal portion of the centering catheter and otherwise remains outside the centering catheter, the guide wire could be fixed to the centering catheter, or the guide wire could be eliminated completely and the centering catheter placed into the pulmonary vein without the aid of a guide wire. Also, the introducer sheath could be withdrawn prior to introducing other catheters, or the centering catheter could be placed into the left atrium without the aid of an introducer sheath.

Note particularly that the ablation catheter could itself be employed as the introducer sheath (particularly where the ablation element is not preformed so as to require a containing sheath), with tools for piercing the septum (if necessary) and centering catheters being introduced through the ablation catheter.

Once the centering catheter 60 is fixed in place, an ablation catheter 50 is advanced over the centering catheter 60 and into the left atrium 122. The ablation element 53 is then opened, expanded, or allowed to expand (as in the case of the illustrated embodiment, in which the ablation element is free to expand once it exits the introducer sheath) within the left atrium 122 in preparation for contacting to the target site for ablation 110 (a region on the atrial wall outside of the pulmonary vein, and surrounding and encircling the opening to the pulmonary vein). At this point, the diameter of the ablation element can be adjusted as described above to conform to the particular pulmonary vein and corresponding ablation site. Since the centering catheter and the ablation catheter are slidably linked, the location of the ablation site and the ability to ablate outside of the pulmonary vein are advantageously enhanced because the ablation site is not dependent on a fixed distance between the ablation element 53 and the distal portion of centering element 62. While the illustrated embodiment employs an ablation catheter in which the centering catheter is received through a lumen along the entire length thereof, it will also be appreciated that the lumen of the ablation catheter could be in a distal portion thereof only, with the centering catheter being positioned external to the body of the ablation catheter along proximal or intermediate portions thereof.

As shown in FIG. 11, after the ablation catheter 50 is introduced into the leatrium and (if necessary) adjusted in diameter, the ablation catheter 50 is then further advanced along the centering catheter 60 until the ablation element 53 contacts the target site for ablation 110, all of which is external to the opening 124 to the pulmonary vein. Ablation of the target site for ablation 110 can then be achieved through the application of an ablation signal or pulse from the power supply to the electrodes (not shown; see FIG. 8), and, if necessary, rotation of the ablation element to achieve a continuous circumferential ablation around the pulmonary vein that isolates the atrial wall surface from the pulmonary vein.

Once the ablation is formed, the respective catheters can be withdrawn from the patient in accordance with usual surgical procedures, and the patient monitored to determine the efficacy of the treatment.

Figure 12:
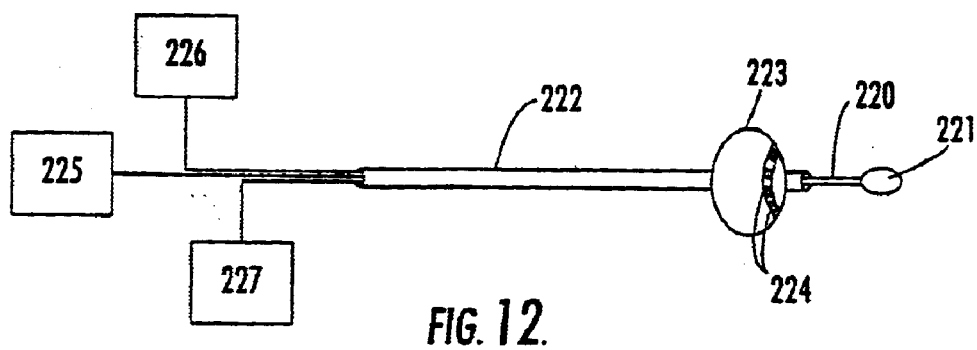
FIG. 12 illustrates an alternate embodiment of the invention in which both the ablation element and the centering element comprise balloons, and in which the centering catheter is a steerable catheter.

While the present invention has been described with respect to particular embodiments above, those skilled in the art will appreciate numerous additional variations that can be made. For example, FIG. 12 illustrates an alternate embodiment of the invention in which both the ablation element and the centering element comprise balloons, and in which the centering catheter is a steerable catheter. The apparatus comprises an centering catheter 220 with a balloon centering element 221 slidably received by an ablation catheter 222 carrying a balloon ablation element 223 having one or (as illustrated) a plurality of electrodes 224 connected to a power supply (not shown). A steering actuator 225 is connected to the centering catheter to steer the distal tip thereof by means such as described above. A first expansion actuator 226 is connected to the centering balloon 221, and a second expansion actuator 227 is connected to the balloon ablation element 223.

Figure 13:
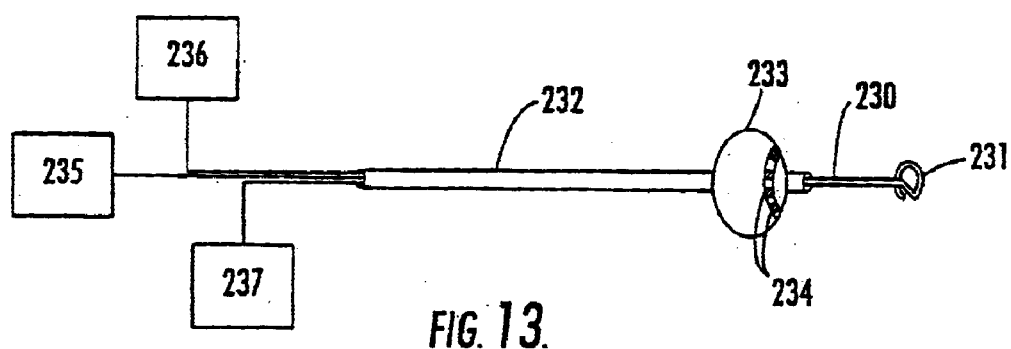
FIG. 13 illustrates an additional embodiment of the invention in which the ablation element is a balloon, the centering element comprises a preformed stylet, and the centering catheter is a steerable catheter.

FIG. 13 illustrates an additional embodiment of the invention in which the ablation element is a balloon, the centering element comprises a preformed stylet, and the centering catheter is a steerable catheter. The apparatus comprises a centering catheter 230 with a preformed centering element 231 slidably received by an ablation catheter 232 carrying a balloon ablation element 233 having one or (as illustrated) a plurality of electrodes 234 connected to a power supply (not shown). A steering actuator 235 is connected to the centering catheter to steer the distal tip thereof by means such as described above. A first expansion actuator 236 is connected to the preformed centering element 231, and a second expansion actuator 237 is connected to the balloon ablation element 233.

Figure 14:
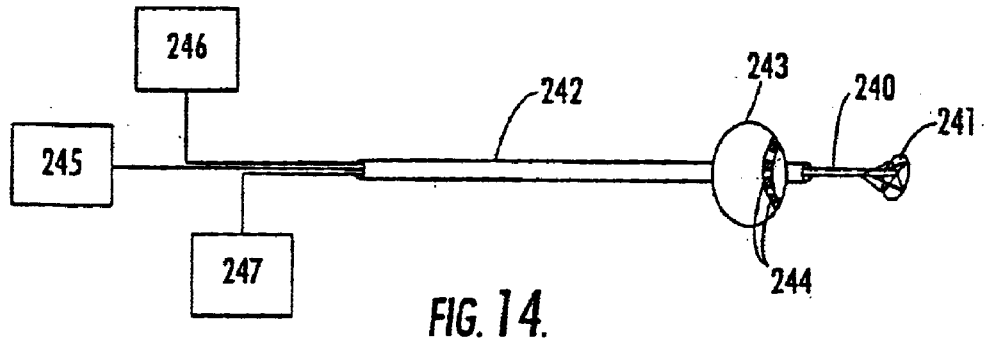
FIG. 14 illustrates an additional embodiment of the invention, in which the ablation element is a balloon, the centering element is a stent, and the centering catheter is a steerable catheter.

FIG. 14 illustrates an additional embodiment of the invention, in which the ablation element is a balloon, the centering element is a stent, and the centering catheter is a steerable catheter. The apparatus comprises an centering catheter 240 with a stent centering element 241 slidably received by an ablation catheter 242 carrying a balloon ablation element 243 having one or (as illustrated) a plurality of electrodes 244 connected to a power supply (not shown). A steering actuator 245 is connected to the centering catheter to steer the distal tip thereof by means such as described above. A first expansion actuator 246 is connected to the centering stent 241, and a second expansion actuator 247 is connected to the balloon ablation element 243.

Figure 15:
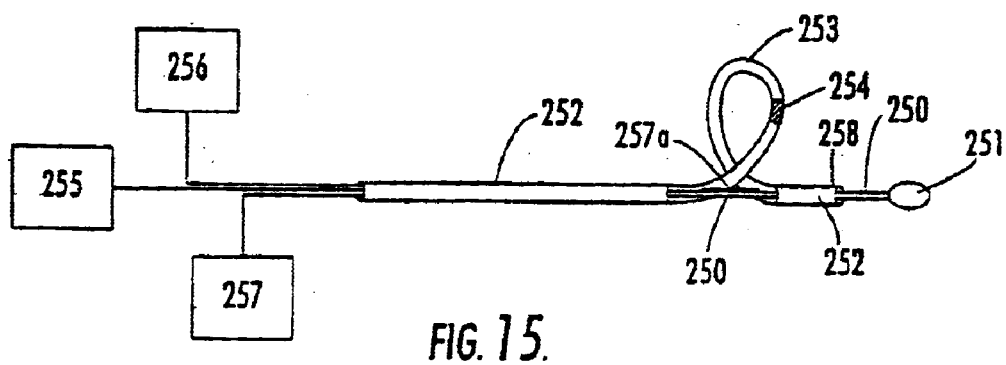
FIG. 15 illustrates an additional embodiment of the invention in which the ablation element is a preformed stylet formed as a single loop, the centering element is a balloon, and the centering catheter is a steerable catheter.

FIG. 15 illustrates an additional embodiment of the invention in which the ablation element is a preformed stylet formed as a single loop, the centering element is a balloon, and the centering catheter is a steerable catheter. The apparatus comprises an centering catheter 250 with a balloon centering element 251 slidably received by an ablation catheter 252 carrying a loop ablation element 253 having an electrode 254 connected to a power supply (not shown). A steering actuator 255 is connected to the centering catheter to steer the distal tip thereof by means such as described above. A first expansion actuator 256 is connected to the centering balloon 251, and a second expansion actuator 257 is connected to the loop ablation element 253. The loop may be a preformed loop, adjustable by means of the expansion actuator 257 operatively associated to a tendon 257a that extends into and is fixed to the distal tip 258 of the ablation catheter, which tendon causes the loop to form when tension is applied.

Figure 16:
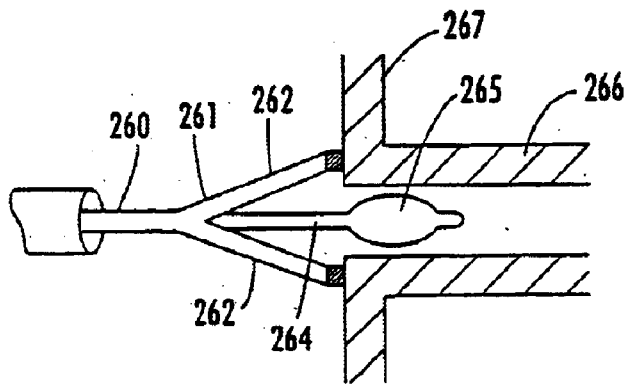
FIG. 16 illustrates an additional embodiment of the invention in which the ablation element is a plurality of expandable legs, each having a distal tip electrode.
Figure 17:
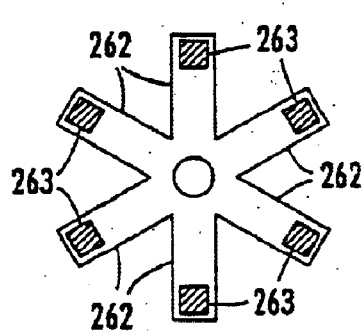
FIG. 17 is an end-on view of an ablation element of FIG. 16.

FIG. 16 and FIG. 17 illustrates an additional embodiment of the invention comprising an ablation catheter 260 having a distal end portion 261, with a plurality of expandable legs 262 serving as an ablation element connected to the distal end portion. The expandable legs can be expanded by means of an actuator or expansion mechanism as described above (e.g., by passing a tendon through the body of the ablation catheter which is in turn connected to tendons extending into each leg in a position so that retraction of the tendon expands or deflects each leg laterally outward), or the legs can be collapsed to a constricted position and passed through an introducer sheath, whereupon the return to an expanded position upon emerging from the introducer sheath as illustrated. Preferably there are at least three or four expandable legs, and there may be up to five, six, eight or ten or more legs. One, a plurality of, or all of the legs have an ablation electrode 263 connected to a distal tip thereof, so that a circumferential ablation is formed upon rotation of the ablation element. A centering catheter 264 over which the ablation catheter is slidably mounted carries a distal balloon 265 as the centering element. Other centering elements as described above could also be used in conjunction with expandable legs as the ablation element. The balloon is positioned with in a vessel 266 entering a wall portion 267 of a heart chamber. The catheter may be implemented in a system as described above, and used in a method as described above.

Figure 18:
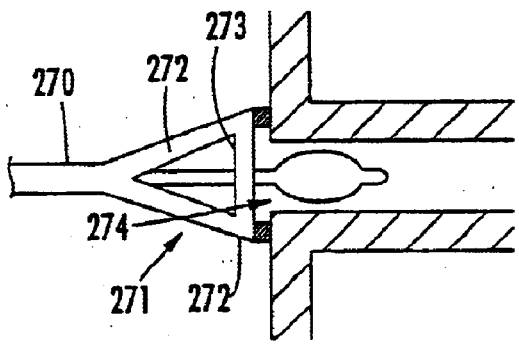
FIG. 18 illustrates an additional embodiment of the invention in which the ablation element is a plurality of expandable legs having an interconnecting bottom portion.

FIG. 18 illustrates an additional embodiment of the invention, similar to that of FIGS. 16–17, in which the ablation element 271 of the catheter 270 comprises a plurality of expandable legs 272 having an interconnecting bottom portion 273. The expandable bottom portion can be made of a compliant, elastic material (metal, polymer, etc. composites thereof), that allows the material to fold along with, or between, the expandable legs. The bottom portion may connect adjacent legs in a circumferential pattern, or may connect opposite legs so that it passes across the opening of the vessel 274.

Figure 19:
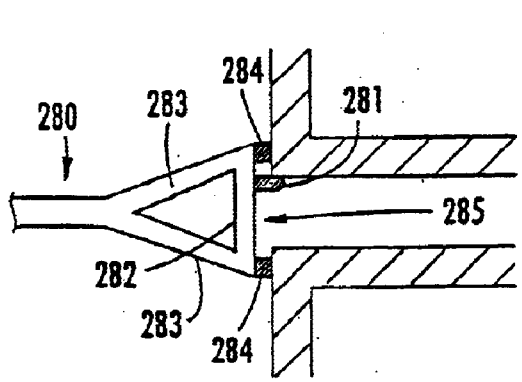
FIG. 19 illustrates a further invention in which the centering element is a nonexpandable, compliant centering element having an outer diameter smaller than the inner diameter of the vessel in which it is positioned. Because the electrodes are configured to form a lesion having an inner diameter sufficiently great that it does not intrude upon the interior of the vessel regardless of where within the vessel the centering element is positioned, the ablation is still formed on the chamber wall outside of the vessel.
Figure 20:
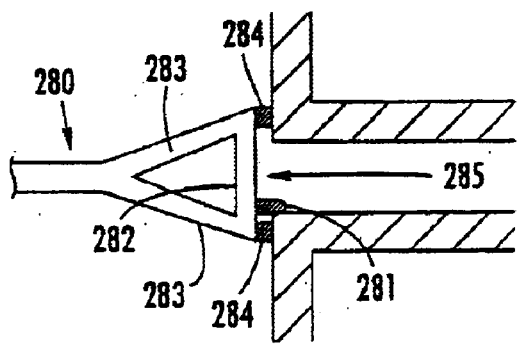
FIG. 20 is an alternate view of the embodiment of FIG. 19, with the centering element shifted to a lower position, showing that the ablation electrodes still remain outside of the vessel.

FIG. 19 and FIG. 20 illustrates a further catheter 280 in which the centering element is a nonexpandable, compliant centering element 281 having outer diameter an not greater than, or even smaller than, the inner diameter of the vessel in which it is positioned. The centering element may be formed of the same types of compliant, flexible materials as the interconnecting bottom portion described above. By "compliant" is meant that the centering element is sufficiently flexible so that it is not unduly hazardous or damaging to the vessel into which it is inserted. The centering element will be of a flexible material that has a memory for its original configuration; that is, it substantially returns to its original configuration when deflected therefrom, to better serve its centering function after being deflected from its original position. The centering element 281 is connected to a bottom portion 282, which is in turn connected to opposite expandable legs 283 carrying electrodes 284 so that the bottom portion passes through the center axis of the catheter and across the opening of the vessel 285. Because the electrodes 284 are configured to form a lesion having an inner diameter sufficiently great so that it does not intrude upon the interior of the vessel regardless of where within the vessel the centering element is positioned (compare the extreme upper position of the centering element within the vessel opening as shown in FIG. 19 with the extreme lower position of the centering element in the vessel opening as shown in FIG. 20), the ablation is still formed on the chamber wall outside of the vessel (by rotation of the catheter, even if the circumferential ablation is not perfectly circular due to lateral movement or wobble of the centering element within the vessel opening). The catheter may be implemented in systems as described above, and employed in methods as described above.

Figure 21:
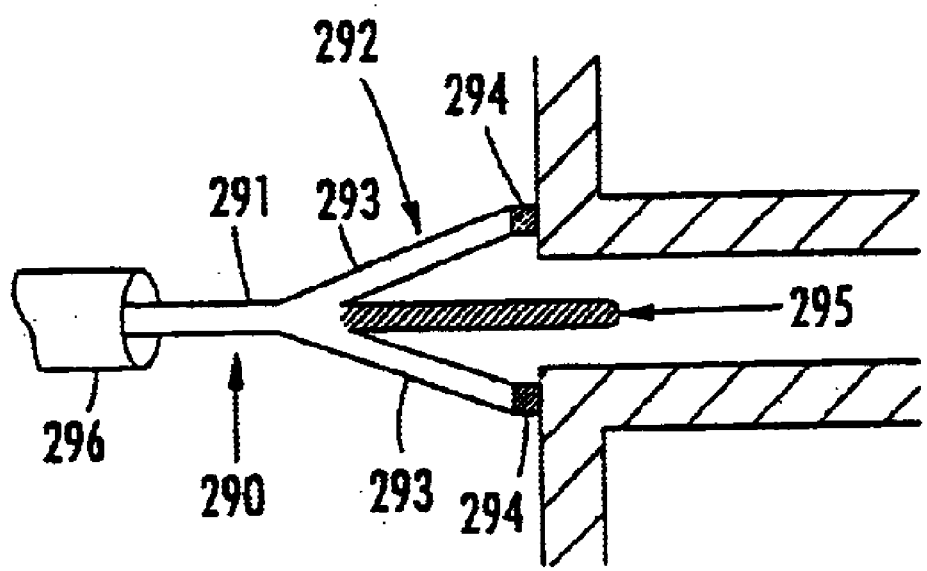
FIG. 21 illustrates a further embodiment of the invention, in which the expandable legs of the ablation element and elastic finger non-expandable, compliant centering element are emerging from an introducer sheath.
Figure 22:
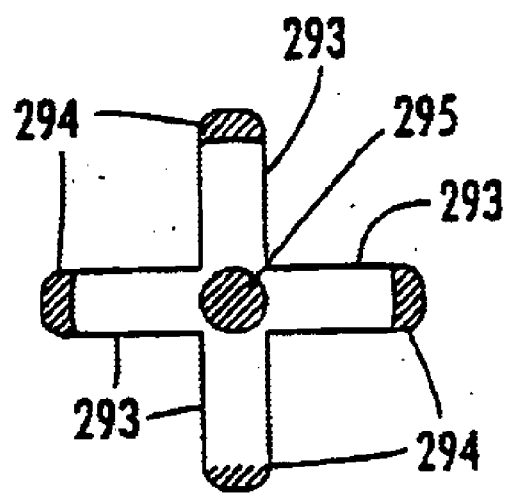
FIG. 22 is an end-on view of the embodiment of FIG. 21.

FIGS. 21 and 22 illustrates a still further catheter 290 of the invention, in which the catheter distal end portion 291 has an ablation element 292 comprised of four expandable legs 293, with each leg having an ablation electrode 294 and the distal end thereof. The centering element comprises a non-expandable, compliant, elastic finger 295, which may be formed as described in connection with the centering element described in FIGS. 19–20 above. The centering element is surrounded by the expandable legs over at least a portion of the length thereof when the legs are in a folded down, collapsed or retracted, position for passing through introducer sheath 296, and which expand into the open, active position upon emerging from the introducer sheath. As noted previously, the legs may be expanded from a collapsed configuration by means of internal tendons as an alternative to, or in addition to, the use of an introducer sheath. As also noted previously, not all legs need carry an ablation electrode. The number of legs may vary depending in part upon the size of the vessel, but there are preferably at least three legs, and may be four, six, or eight or more legs. A bottom portion as described above may be added to provide further structural rigidity to the legs when they are in the open position. Any of the features described above may be incorporated into the catheter, including but not limited to a steering stylet and a steering tendon operatively associated with said steering stylet for steering the catheter into the desired location. Again, the catheter may be incorporated into systems as described above and used in methods as described above.

The foregoing is illustrative of the present invention, and is not to be construed as limiting thereof. The invention is defined by the following claims, with equivalents of the claims to be included therein.

That which is claimed is:

1. A cardiac ablation apparatus for producing a circumferential ablation that electrically isolates a chamber wall portion of a heart from a vessel extending into said wall portion, said apparatus comprising:
    (a) an elongate centering catheter having a distal end portion;
    (b) a guide wire, wherein said centering catheter is slidably received on said guide wire;
    (c) an expandable centering element connected to said centering catheter distal end portion and configured for positioning within said vessel when in a retracted configuration, and for securing said elongate centering catheter in a substantially axially aligned position with respect to said vessel when said centering element is in an expanded configuration;
    (d) an ablation catheter slidably received on said centering catheter, said ablation catheter having a distal end portion, and
    (e) an expandable ablation element connected to said ablation catheter distal end portion, said ablation element configured to form a circumferential ablation on said wall portion around said elongate centering catheter when said centering catheter is axially aligned with respect to said vessel.

2. A cardiac ablation apparatus according to claim 1, wherein said centering element comprises a balloon.

3. A cardiac ablation apparatus according to claim 1, wherein said ablation element comprises a preformed stylet.

4. A cardiac ablation system for producing a circumferential ablation that electrically isolates a chamber wall portion of a heart from a vessel extending into said wall portion, said system comprising:
    (a) an elongate centering catheter having a distal end portion;
    (b) a guide wire, wherein said centering catheter is slidably received on said guide wire;
    (c) an expandable centering element connected to said centering catheter distal end portion and configured for positioning within said vessel when in a retracted configuration, and for securing said elongate centering catheter in a substantially axially aligned position with respect to said vessel when said centering element is in an expanded configuration;
    (d) an ablation catheter slidably received on said centering catheter, said ablation catheter having a distal end portion; and
    (e) an expandable ablation element connected to said ablation catheter distal end portion, said ablation element configured to form a circumferential ablation on said wall portion around said elongate centering catheter when said centering catheter is axially aligned with respect to said vessel; and
    (f) a power supply operably associated with said ablation element.

5. A cardiac ablation system according to claim 4, wherein said centering element comprises a balloon.

6. A cardiac ablation system according to claim 4, wherein said ablation element comprises a preformed stylet.

7. A cardiac ablation system according to claim 4, wherein said power supply comprises a radio frequency ablation power supply.

8. A cardiac ablation system according to claim 4, wherein said power supply comprises a thermal ablation power supply.

9. A cardiac ablation system according to claim 4, further comprising a first expansion actuator operatively associated with said centering element.

10. A cardiac ablation system according to claim 9, further comprising a second expansion actuator operatively associated with said ablation element.

11. A cardiac ablation method for producing a circumferential ablation that electrically isolates a chamber wall portion of a heart from a vessel extending into said wall portion, said method comprising the steps of:
    (a) inserting an elongate centering catheter having a distal end portion through an chamber into said vessel with a guide wire, said distal end portion having an expandable centering element for engaging said vessel connected thereto;
    (b) expanding said centering element in said vessel to secure said elongate centering catheter in a substantially axially aligned position with respect to said vessel; then
    (c) inserting an ablation catheter slidably received on said centering catheter into said chamber, said ablation catheter having an expandable ablation element connected to the distal end portion thereof; then
    (d) positioning said ablation element on said chamber wall portion; and then
    (e) forming a circumferential ablation around said elongate centering catheter on said wall portion in said chamber and outside of said vessel.

12. A method according to claim 11, wherein the inner diameter of said circumferential ablation is greater than the inner diameter of said vessel.

13. A method according to claim 11, further comprising the step of adjusting the diameter of said ablation element after inserting said ablation catheter into said chamber, and before forming said circumferential ablation.

14. A method according to claim 11, wherein said chamber is an atrium and said vessel is a pulmonary vein.

15. A cardiac ablation apparatus for producing a circumferential ablation that electrically isolates a chamber wall portion of a heart from a vessel extending into said wall portion, said apparatus comprising:
    (a) an elongate centering catheter having a distal end portion and a steering stylet and a steering tendon operatively associated with said steering stylet;
    (b) an expandable centering element connected to said centering catheter distal end portion and configured for positioning within said vessel when in a retracted configuration, and for securing said elongate centering catheter in a substantially axially aligned position with respect to said vessel when said centering element is in an expanded configuration;
    (c) an ablation catheter slidably received on said centering catheter said ablation element having a distal end portion, and
    (d) an expandable ablation element connected to said ablation catheter distal end portion, said ablation element configured to form a circumferential ablation on said wall portion around said elongate centering catheter when said centering catheter is axially aligned with respect to said vessel.

16. A cardiac ablation apparatus according to claim 15, wherein said centering element comprises a balloon.

17. A cardiac ablation apparatus according to claim 15, wherein said ablation element comprises a preformed stylet.

18. A cardiac ablation system for producing a circumferential ablation that electrically isolates a chamber wall portion of a heart from a vessel extending into said wall portion, said system comprising:

(a) an elongate centering catheter having a distal end portion;

(b) an expandable centering element connected to said centering catheter distal end portion and configured for positioning within said vessel when in a retracted configuration, and for securing said elongate centering catheter in a substantially axially aligned position with respect to said vessel when said centering element is in an expanded configuration, said centering cather comprising a steering stylet and a steering tendon operatively associated with said steering stylet;

(c) a steering mechanism operatively associated with said steering tendon and steering stylet;

(d) an ablation catheter slidably received on said centering catheter, said ablation catheter having a distal end portion; and (e) an expandable ablation element connected to said ablation catheter distal end portion, said ablation element configured to form a circumferential ablation on said wall portion around said elongate centering catheter when said centering catheter is axially aligned with respect to said vessel; and (f) a power supply operably associated with said ablation element.

19. A cardiac ablation system according to claim 18, wherein said centering element comprises a balloon.

20. A cardiac ablation system according to claim 18, wherein said ablation element comprises a preformed stylet.

* * * * *